(12) United States Patent
Mazur

(10) Patent No.: US 8,069,774 B2
(45) Date of Patent: Dec. 6, 2011

(54) WATER PURIFIER AND COOLER, BOTTLE AND CAP CLEANER, AND WATER FILLER AND NUTRIENT MIXER

(76) Inventor: Robert Mazur, Canton, MI (US)

(*) Notice: Subject to any disclaimer, the term of this patent is extended or adjusted under 35 U.S.C. 154(b) by 807 days.

(21) Appl. No.: 12/059,083

(22) Filed: Mar. 31, 2008

(65) Prior Publication Data

US 2008/0260907 A1    Oct. 23, 2008

Related U.S. Application Data

(60) Provisional application No. 60/921,087, filed on Mar. 30, 2007.

(51) Int. Cl.
*A47J 31/00* (2006.01)

(52) U.S. Cl. ........... 99/275; 99/289 R; 222/129.1; 222/190; 222/566; 141/137; 141/237; 141/238; 141/270; 141/272; 141/275

(58) Field of Classification Search ........... 99/289 R, 99/275; 222/129.1, 142, 138, 146.1, 146.2, 222/566, 61, 63, 190; 141/235, 237, 238, 137, 272, 275, 270, 266, 283, 284
See application file for complete search history.

(56) References Cited

U.S. PATENT DOCUMENTS

| | | | | | |
|---|---|---|---|---|---|
| 3,915,207 | A | * | 10/1975 | Greenfield et al. | 141/82 |
| 4,184,523 | A | * | 1/1980 | Carrigan et al. | 141/238 |
| 4,655,029 | A | * | 4/1987 | Weiss | 53/432 |
| 5,531,057 | A | * | 7/1996 | Coleman et al. | 53/308 |
| 5,881,913 | A | * | 3/1999 | Boulter | 222/2 |
| 6,095,205 | A | * | 8/2000 | Nagasawa | 141/89 |
| 6,668,877 | B2 | * | 12/2003 | Fehland et al. | 141/70 |
| 7,617,849 | B2 | * | 11/2009 | Dubois et al. | 141/83 |

* cited by examiner

*Primary Examiner* — Reginald L Alexander
(74) *Attorney, Agent, or Firm* — Brinks Hofer Gilson & Lione

(57) ABSTRACT

An automated apparatus that sterilizes and refills beverage containers with filtered water and any number of additives or ingredients such as nutrients, health supplements, caffeine, flavorings, vitamins, sweeteners, coloring agents, medicines, etc. The apparatus allows consumers, including home consumers, to produce, customize and "bottle" their own flavored and fortified filtered water.

19 Claims, 12 Drawing Sheets

WATER PURIFIER AND COOLER, BOTTLE AND CAP CLEANER, AND WATER FILLER AND NUTRIENT MIXER

RELATED APPLICATION

The present application is based upon U.S. provisional patent application Ser. No. 60/921,087, filed on Mar. 30, 2007, to which priority is claimed under 35 U.S.C. §120, the complete disclosure of which is expressly incorporated herein by reference.

TECHNICAL FIELD

The present invention relates to an appliance and system for providing clean filtered water for consumers and optionally

BACKGROUND ART

The popularity of non-carbonated, non-alcoholic beverages, particularly flavored and fortified filtered water has been increasing steadily over the past few years. The demand for flavored and fortified filtered water together with brand name marketing has resulted in significant costs for flavored and fortified filtered water, the basic component of which is filtered or distilled water.

Concerns as to the purity and accuracy of the source of such water-based beverages have led to the finding that in some cases, exotic brand named varieties are nothing more than filtered municipal tap water.

The present invention is directed to an automated apparatus that conveniently refills containers with filtered water and any number of additives or ingredients such as nutrients, health supplements, caffeine, flavorings, vitamins, sweeteners, coloring agents, medicines, etc. This automated apparatus allows consumers, including home consumers, to produce, customize and "bottle" their own flavored and fortified filtered water.

DISCLOSURE OF THE INVENTION

According to various features, characteristics and embodiments of the present invention which will become apparent as the description thereof proceeds, the present invention provides a method of producing a water-based beverage which method involves:

providing a first dispenser for dispensing at least one of an ingredient selected from the group consisting of nutrients, health supplements, caffeine, flavorings, vitamins, sweeteners, coloring agents and medicines into a container;

providing a second dispenser for dispensing water in a container;

providing a capping mechanism for putting a cap on a container;

providing at least one container on a support base;

moving one of the support base and the so that the at least one container is at the first station and dispensing at least one of nutrients, health supplements, caffeine, flavorings, vitamins, sweeteners, coloring agents and medicines into the at least one container;

moving at least one of the support base and the first dispenser so that the at least one container is aligned with the first dispenser and dispensing one of the ingredients into the at least one container;

moving at least one of the support base and the second dispenser so that the at least one container is aligned with the second dispenser and dispensing water into the at least one container; and moving at least one of the support base and the capping mechanism so that the at least one container is aligned with the capping mechanism and putting a cap on the at least one container.

The present invention further provides for an apparatus producing a water-based beverage that includes:

a first dispenser for dispensing coupled to a source of at least one of an ingredient selected from the group consisting of nutrients, health supplements, caffeine, flavorings, vitamins, sweeteners, coloring agents and medicines;

a second dispenser coupled to a source of water;

a container capping mechanism including a supply of container caps;

at least one container on a support base;

means for moving at least one of the support base and the first dispenser so that the at least one container is aligned with the first dispenser for dispensing one of the ingredients into the at least one container;

means for moving at least one of the support base and the second dispenser so that the at least one container is aligned with the second dispenser for dispensing water into the at least one container; and means for moving at least one of the support base and the capping mechanism so that the at least one container is aligned with the capping mechanism for putting a cap on the at least one container.

BRIEF DESCRIPTION OF DRAWINGS

The present invention will be described with reference to the attached drawings which are given as non-limiting examples only, in which.

BEST MODE FOR CARRYING OUT THE INVENTION

The present invention is directed to an automated apparatus that conveniently refills containers with filtered water and any number of additives or ingredients such as, but not limited to, nutrients, health supplements, caffeine, flavorings, vitamins, sweeteners, coloring agents, medicines, etc. The automated apparatus of the present invention allows consumers, including home consumers, to produce, customize and "bottle" their own flavored and fortified filtered water The apparatus includes an ingredient dispenser or dispensing station for dispensing at least one of an ingredient such as, but not limited to nutrients, health supplements, caffeine, flavorings, vitamins, sweeteners, coloring agents, medicines, etc. into one or more containers. The ingredient dispenser can be provided on a carrier that moves with respect to a support base which supports a plurality of containers to be filled. Otherwise the ingredient dispenser can be provided as a stationary station at which the containers to be filled are presented.

The apparatus includes a water dispenser coupled to a source of water for filling containers. The source of water can be a water reservoir provided in a housing of the apparatus. The water reservoir can be filled with water from a filling container that is filtered in the apparatus. Alternatively, the apparatus can be connected to a source of water via a water supply line or conduit.

The apparatus includes a container capping mechanism that can be configured to attach threaded caps onto the containers or other types of caps such as snap-on caps, press-on caps, etc.

Containers that are to be filled with water-based beverages according to the present invention are supported in or on a support base. One of at least the support base and each of the ingredient dispenser, water dispenser and capping mechanism can be moved relative to the other so that the containers on the support base can be aligned consecutively with: the ingredient dispenser for dispensing one of the ingredients into the containers; the water dispenser for dispensing water into the containers; and the capping mechanism so that caps can be put on the containers. According to one embodiment the containers are held in fixed positions on the support base. According to another embodiment the containers move about the support base.

The apparatus can be designed and configured to be positioned on a counter top, table, shelf, etc. In other embodiments the apparatus can be designed and configured to be stored or built into a refrigerator or a vehicle or can be designed and configured to be a portable apparatus.

A plurality of UV light sources are provided in different positions of the apparatus to sterilize the containers and water held in the water reservoir.

Figure 1:
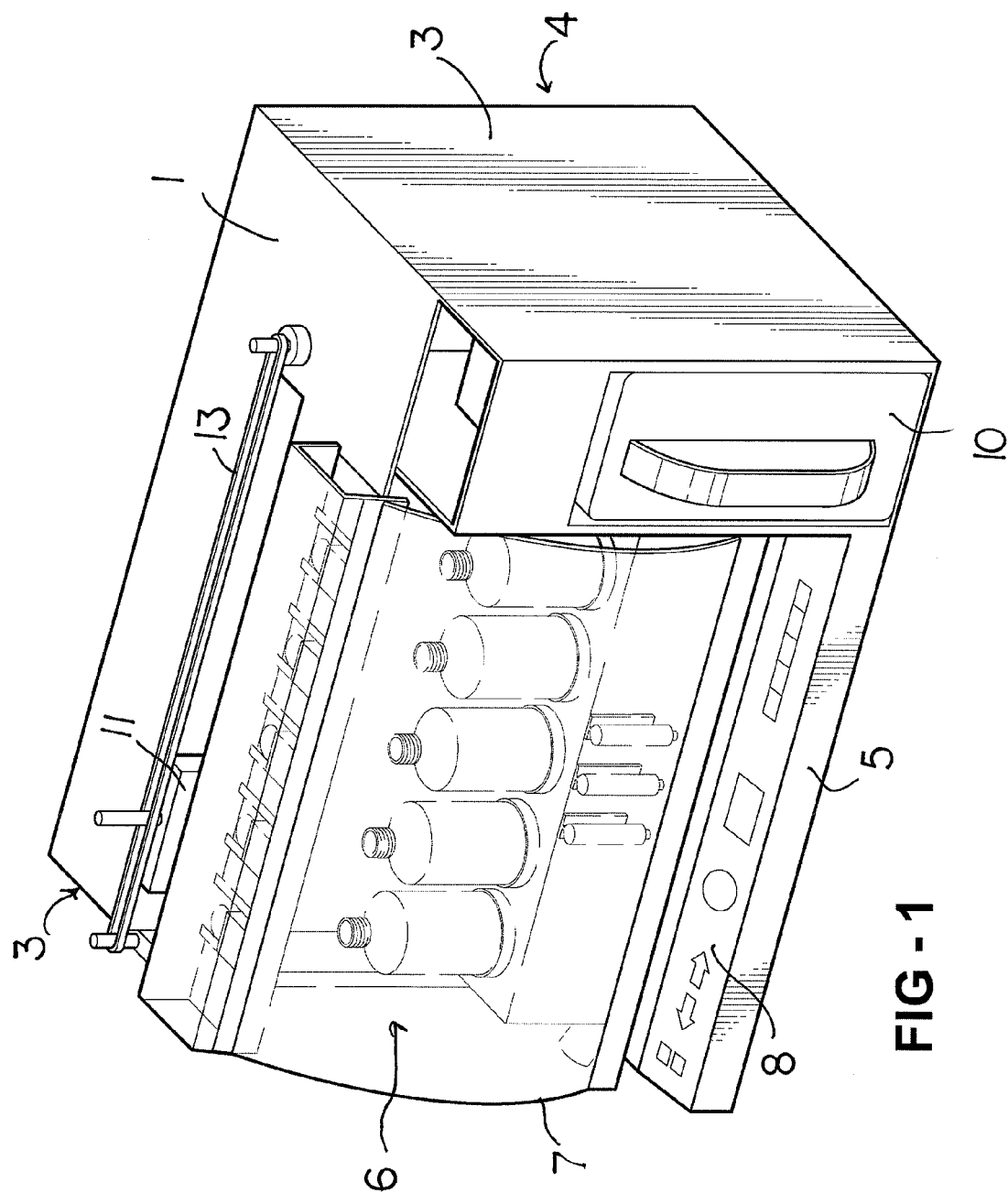
FIG. 1 is a perspective view of an apparatus according to one embodiment of the present invention.

FIG. 1 is a perspective view of an apparatus according to one embodiment of the present invention. The embodiment of the invention depicted in FIG. 1 includes a housing having a top 1, bottom 2 opposite sides 3, back 4 and front 5. The front 5 includes a dispensing chamber 6 that is closed by a cover 7.

The cover 7 can be transparent or semitransparent in whole or in part as desired to allow for observation into the dispensing chamber 6. According to one embodiment of the present invention that utilizes UV radiation within the dispensing chamber 6 for sterilization, the cover 7 can be made of a material that shields against UV radiation to protect consumer exposure. The front 5 also includes a control panel 8 and a compartment 9 for removably storing a filling container 10 therein.

The embodiment of the invention depicted in FIG. 1 is designed and configured to be positioned on a counter top, table, shelf, etc. In other embodiments the apparatus can be designed and configured to be stored or built into a refrigerator or a vehicle or can be designed and configured to be a portable apparatus. As such, the configuration, design and placement of various elements such as the cover 7 control panel 8, filling container 10, etc. can be varied without departing from the scope of the present invention.

A carrier 11 is shown as extending through a slot 12 provided at the top 1 of the housing. The carrier 11 is moved linearly by a belt 13 that is driven by a stepper motor (not shown). In alternative embodiment, the carrier 11 can be contained beneath the top 1 of the housing and otherwise driven or moved linearly by any convenient mechanical or electromechanical means, including linear actuators such as a threaded rod coupled to the carrier 11, a chain driven mechanism, etc.

The apparatus can be power by a standard household current and include a conventional plug-in cord (not shown) for such purposes. Alternatively, the apparatus can be powered by a battery or battery pack (not show) that is contained within the housing, or can include a back-up battery or battery pack.

Water can be supplied to the apparatus by removing filling container 10 and filling the container 10 with water and pouring the water from filling container 10 into the water inlet 14 provided on the top 1 of the apparatus housing. Alternatively, a water supply line (not shown) could be connected between the apparatus and a source of water such as a household or commercial plumbing system.

Figure 2:
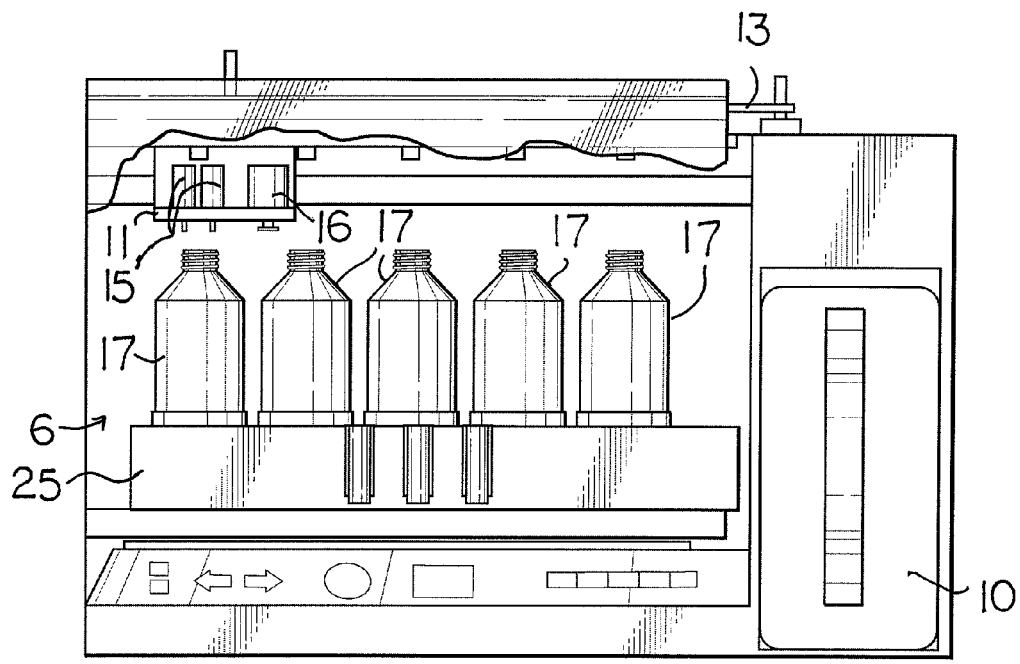
FIG. 2 is a front planar view of the apparatus of FIG. 1 showing details of the elements within the dispensing chamber.

FIG. 2 is a front planar view of the apparatus of FIG. 1 showing details of the elements within the dispensing chamber. The carrier 11 shown in FIG. 2 supports one or more cylinders or cartridges 15 (two shown) and a VU light source 16. The cylinders or cartridges 15 are replaceable and can contain nutrients, flavorings, vitamins, sweeteners, caffeine, health supplements, coloring agents, medicines, etc. in the form of liquids, solids or gases which are selectively dispensed into containers 17. Containers 17 are supported within dispensing chamber 6 and can be aligned beneath carrier 11 and hence cylinders or cartridges 15 and VU light source 16 as carried moves linearly within the dispensing chamber 6. It is noted that UV light source 16 or an additional UV light source can be provided at any desired location within dispensing chamber 6. In particular, a UV light source 16 is provided which directs UV light into the filtered water reservoir 18 located below the dispensing chamber 6. The UV light sources 16 can be designed for easy removal for replacement or for changing the bulbs. For example the UV light sources 16 can include bulb holders that can be plugged into receptacles, bayonet-type mounts, twist and lock mounts, threaded mounts, etc.

Figure 3:
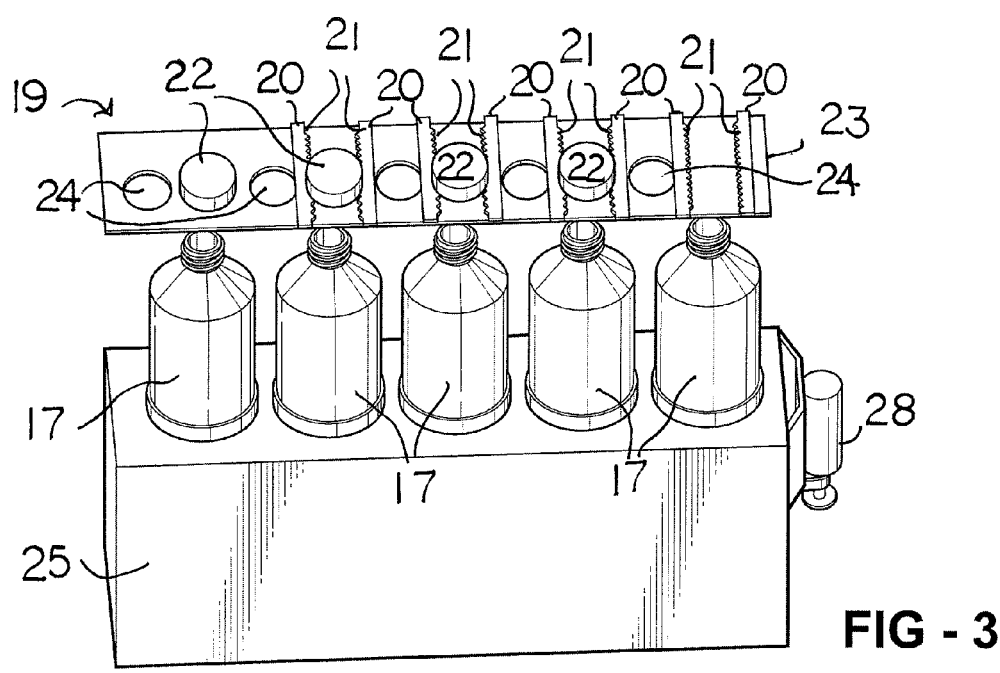
FIG. 3 is a perspective view of a cap retaining mechanism according to one embodiment of the present invention.

FIG. 3 is a perspective view of a cap retaining mechanism according to one embodiment of the present invention. The cap retaining mechanism 19 includes a plurality of opposed cap retaining jaw elements 20 than have inward facing gripping surfaces 21. In use, screw on or threaded caps 22 are manually positioned between opposed pairs of the retaining jaw elements 20 as depicted. The retaining jaw elements 20 are provided over a sliding base element 23 which includes through-holes 24 that have a diameter which is equal to or slightly larger than the outer diameter of the caps 22. After the caps 22 are positioned between opposed pairs of the retaining jaw elements 20, the sliding base element 23 can be slide in the direction of arrow "a" so that the through-holes 24 are aligned and beneath caps 22. In this alignment, the caps 2 can be threaded onto containers 17 as discussed in more detail below. The jaw elements 20 can be made of a rubber material, a metal such as steel, or any other material that will hold caps 22 in a frictional and/or mechanical, or electro mechanical manner. The sliding base element 23 can be slid manually or automatically using any conventional mechanical or electro mechanical means.

Figure 5:
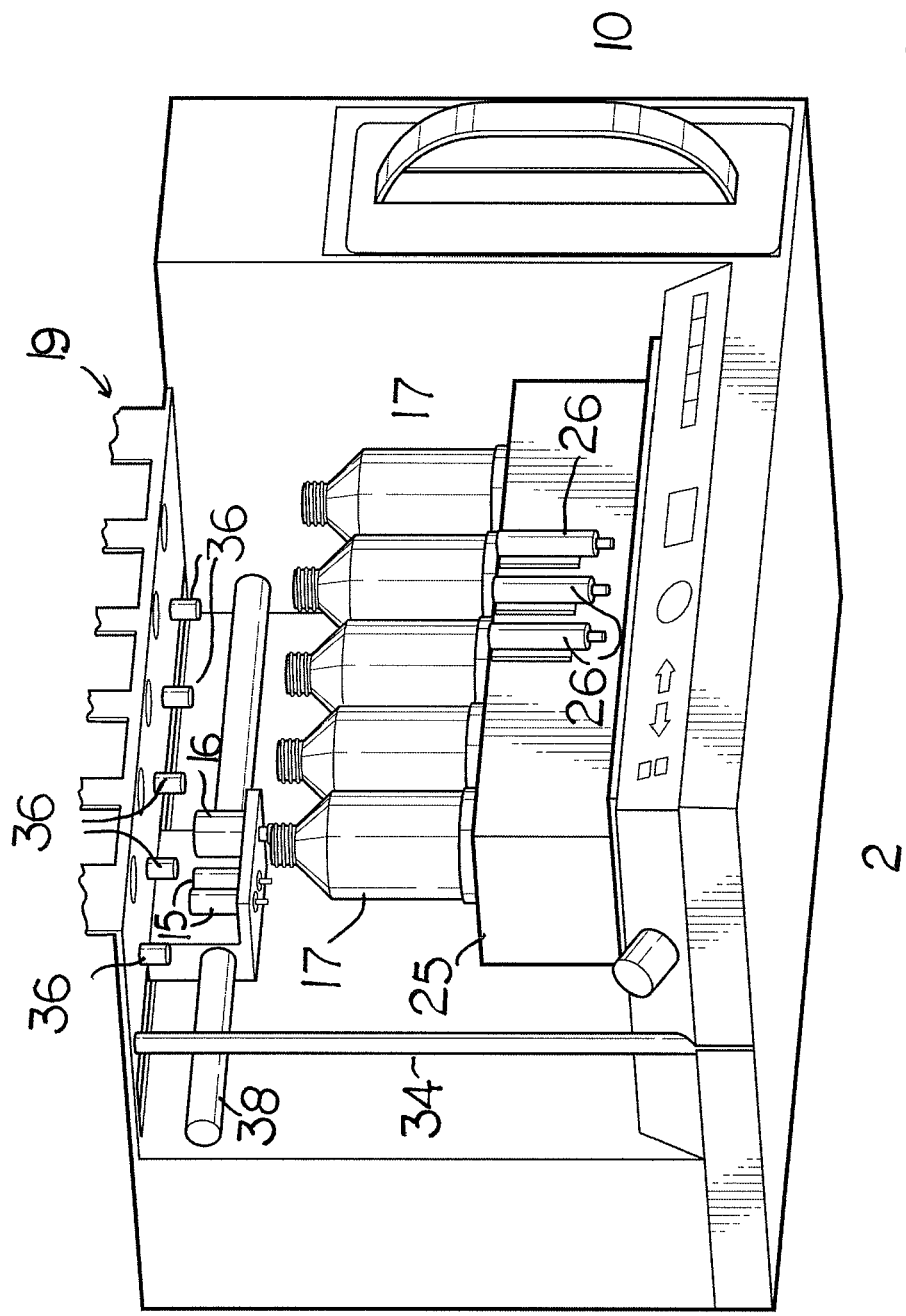
FIG. 5 is a perspective view of the elements in the dispensing chamber of the apparatus of FIG. 1.

The containers 17 are held by support base 25 which has a plurality of solenoids 26 on one side of the support base 25 (See FIG. 5). These solenoids 26 have different length rods that can be extended when the solenoids 26 are actuated. The different length rods will allow the support base 25 to rise to different heights and inclined at different angles as will be understood as the description of the invention proceeds. A pair of additional solenoids 27 are provided on the opposite side of the support base 25 near opposite ends there of. Solenoids 26 and 27 are used to raise and tilt the support base 25 as discussed below. As will be described in detail below, a motor 28 is provided on one end of the support base 25, which motor 28 drives a belt 29 that passes beneath the support base 25. As further described in more detail below, containers 17 are held in container receivers 30 that configured to rotate as described in detail below.

Figure 4:
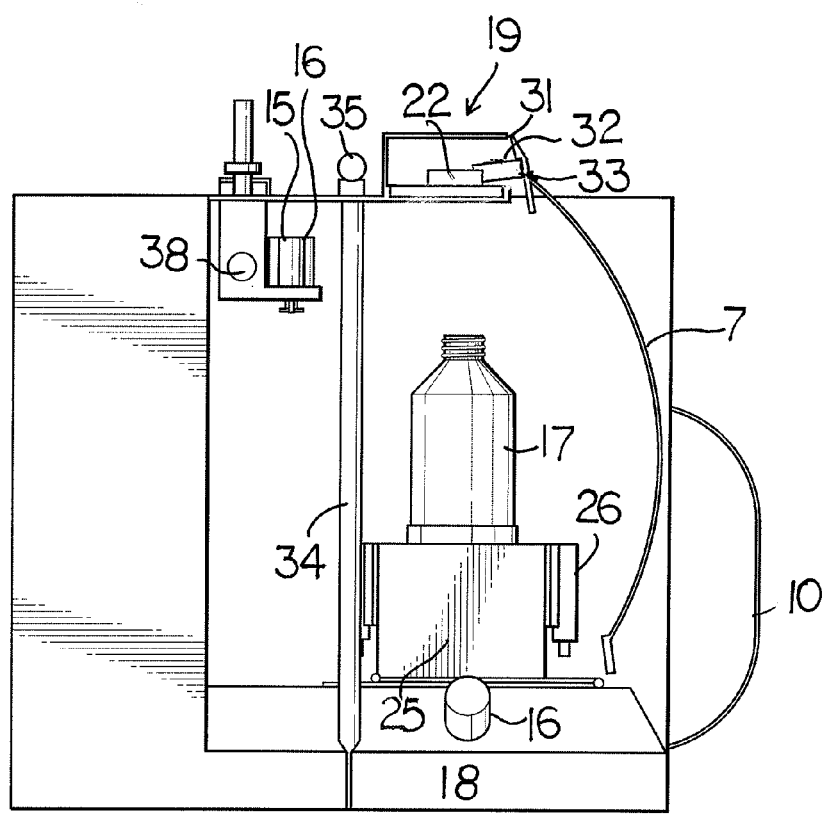
FIG. 4 is an end view of the apparatus of FIG. 1.

FIG. 4 is an end view of the apparatus of FIG. 1. As shown in FIG. 4, the cover 7 is coupled to an upper hinge 31 by a bracket 32 which is coupled to a protrusion 33 that presses downward on caps 22 when the cover 7 is pivoted into its closed position. As noted above, a filtered water reservoir 18 is provided beneath the dispensing chamber 6. A fluid transfer tube or conduit 34 is provided within the apparatus housing which provides fluid communication between the filtered water reservoir 18 and a fluid dispensing manifold 35 that distributes filtered water to fluid dispensing spouts 36 which are discussed below. A pump 37 is provided which, when activated, pumps filtered water from filtered water reservoir 18 through fluid transfer tube or conduit 34 and manifold 35 and eventually into containers 17. In an alternative embodiment the filtered water can be transferred from filtered water reservoir 18 upwards through fluid transfer tube or conduit 34 by heating the fluid in a manner that is conventionally used in drip type coffee makers.

FIG. 5 is a perspective view of the elements in the dispensing chamber of the apparatus of FIG. 1. The carrier 11 is shown as being guided or slidable along carrier rod 38. The carrier 11 is operable to slide or be positioned along carrier rod 38 so as to be aligned with any one of the containers 17. In addition, it is possible, if desired, to provide an extended carrier rod 38 and position the carrier 11 off to the side of the containers 17.

A plurality of filtered water dispensing spouts 36 are provided above the heights of containers 17. These filtered water dispensing spouts 36 are in fluid communication with manifold 35 shown in FIG. 4 and discussed above.

Figure 6:
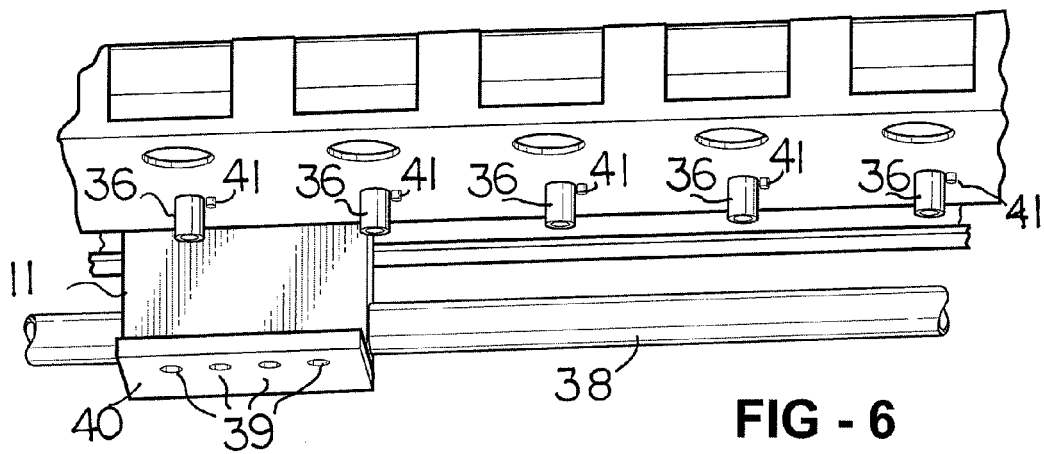
FIG. 6 is an enlarged perspective view of the carrier and filtered water dispensing spouts according to one embodiment of the present invention.

FIG. 6 is an enlarged perspective view of the carrier and filtered water dispensing spouts according to one embodiment of the present invention. The carrier 11 is shown as having a plurality of through-holes 39 in the base 40 thereof. These through-holes 39 are configured to receive the cylinders or cartridges 5 and a VU light source 16 discussed above and shown in FIG. 2. In other embodiments the coupling or securing of the cylinders or cartridges 15 to the carrier 11 can be accomplished by means such as slots, hooks, clips, cooperating structures similar to those conventionally used on of the carriers for printer ink cartridges, bayonet coupling structures, threaded coupling structures, etc. Each of the filtered water dispensing spouts 36 is provided with a fluid level sensor 41 that is used to control the dispensing of filtered water into containers 17 to a predetermined level, e.g. so that the containers 17 are not overfilled. These sensors 41 can be sound sensors that recognize the change in pitch as the liquid level rises within containers 17. In an alternative embodiment, the sensors 41 can be distance measuring devices, e.g. laser devices that measure the height of the liquid surface in the containers 17. In other embodiments sensors 41 could measure frequency much like how radar functions where electromagnetic radiation is reflected from the liquid surface in the containers 17. Other types of sensors that could be used include conductance sensors, pressure sensors, or any suitable type of sensor. The sensors 41, in conjunction with a control system or unit (e.g. CPU), close valves associated with the filtered water dispensing spouts 36 to prevent over- and under-filling of the containers 17.

Figure 7:
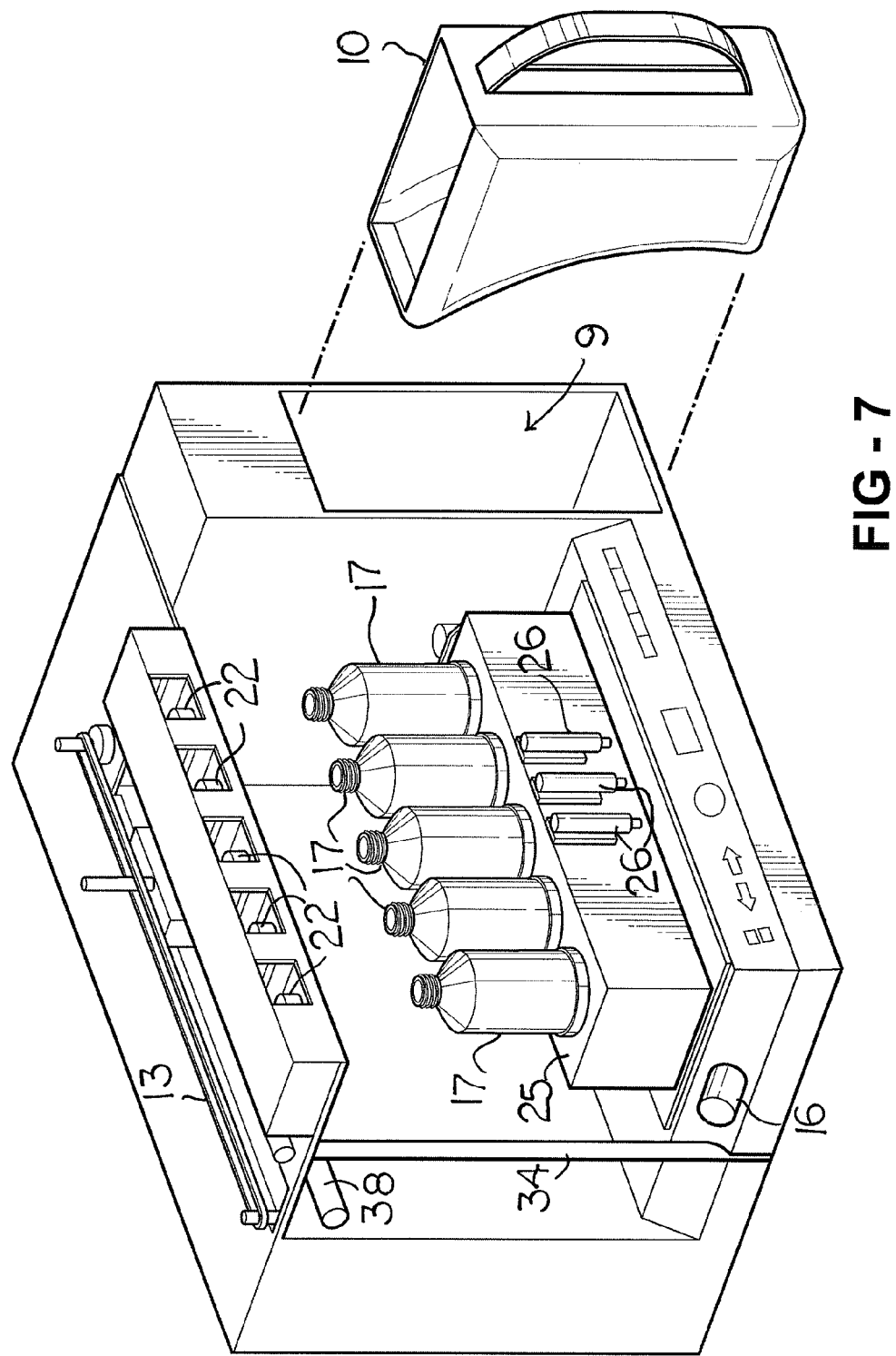
FIG. 7 is a perspective view of the apparatus of FIG. 1 with the cover of the dispensing chamber removed.

FIG. 7 is a perspective view of the apparatus of FIG. 1 with the cover of the dispensing chamber removed. FIG. 7 shows the filling container 10 removed from its storage compartment 9. The filling container 10 can be removed from storage compartment 9 and used to fill the reservoirs within the apparatus housing via the water inlet 14. One of reservoirs provide within the apparatus housing is a filtered water reservoir 18 that is located beneath the dispensing chamber 6 and below support base 25. A UV light source 16 is provided which directs UV light into the filtered water reservoir 18 to sterilize the filtered water therein.

Figure 8:
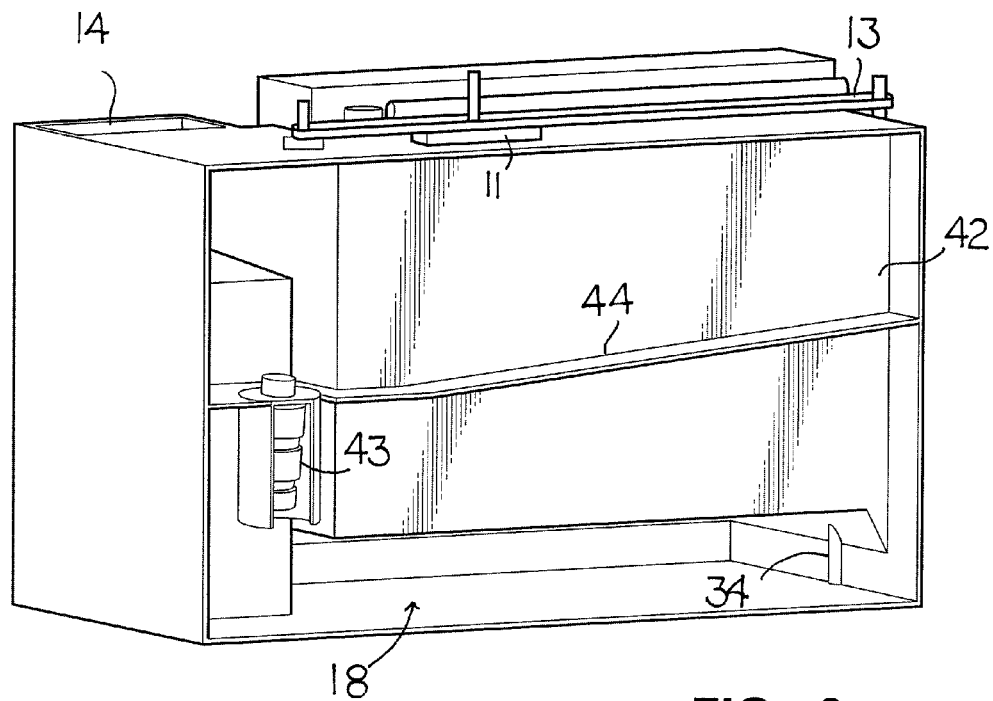
FIG. 8 is a cut-away perspective view of the back side of the apparatus of FIG. 1.

FIG. 8 is a cut-away perspective view of the back side of the apparatus of FIG. 1. As shown, the housing contains a filtered water reservoir 18 in a lower portion and an unfiltered water reservoir 42 above the filtered water reservoir 18. In use, water is poured into the unfiltered water reservoir 42 through water inlet 14. The unfiltered water passes from the unfiltered water reservoir 42 through filter cartridge 43 into the filtered water reservoir 18. For this purpose, the bottom 44 of the unfiltered water reservoir 42 is slopped toward the filter cartridge 43. The filter cartridge 43 is a replaceable filter cartridge 43 and can be replaced via an access door (not shown) that can be provided in any convenient location such as the top 1 or back 4 of the housing. In FIG. 8, the UV light source 16 can be seen as well as the lower portion of the fluid transfer tube or conduit 34.

Figure 9:
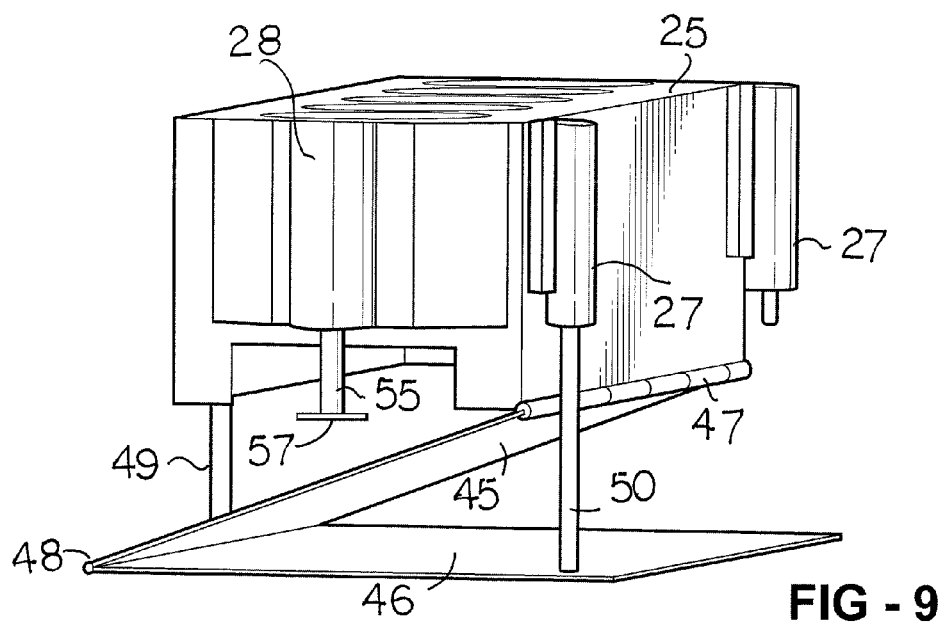
FIG. 9 is an enlarged perspective view of a portion of the support base that holds the containers.

FIG. 9 is an enlarged perspective view of a portion of the support base that holds the containers. The support base 25 is designed to lift and angle the containers 17 supported thereon in various heights and at different angles. To achieve the desired lifting and angling, the support base is coupled to the bottom of the apparatus by an upper hinge plate 45 and a lower hinge plate 46 by hinges 47 and 48. As shown in FIG. 9, the solenoids 26 and 27 can be operated to lift and angle the support base 25. For example, when one of the solenoids 26 on the front of the support base 25 is activated, the end of the rod 49 of that solenoid presses against the upper hinge plate 45 (or the bottom of the housing) can cause the support base 25 to rise upward. At the same time, the pair of solenoids 27 on the other side of the support base 25 can be activated so that the end of the rods 50 of those solenoids press against the lower hinge plate 46. As can be understood from FIG. 9, the height at which the support base 25 can be lifted can be controlled by cooperation or co-operation (or co-activation) of the solenoids 26 and 27. Moreover, the angle at which the support base 25 pivots about hinge 47 can also be adjusted. In this regard, FIG. 9 illustrates a position in which the support base 25 is lifted above upper hinge plate 45 (and the bottom of the housing) and is substantially level. However, if a solenoid 26 were activated at the front of the support base 25 that had a longer rod 49, it can be understood from FIG. 9 that the font side of the support base 25 would be higher than the back side so that the support base 25 would be lifted and aligned at an angle so that containers 17 supported thereon would lean towards the back of the dispensing chamber 6. The present invention is not specifically limited to the use of solenoids 26 and 27 to lift and incline the support base 25 or hinge plates 47 and 18. In other embodiments various combinations of motors, levers, pulleys, cams and other electro mechanical means can be used to raise and incline the support base 25.

Figure 10:
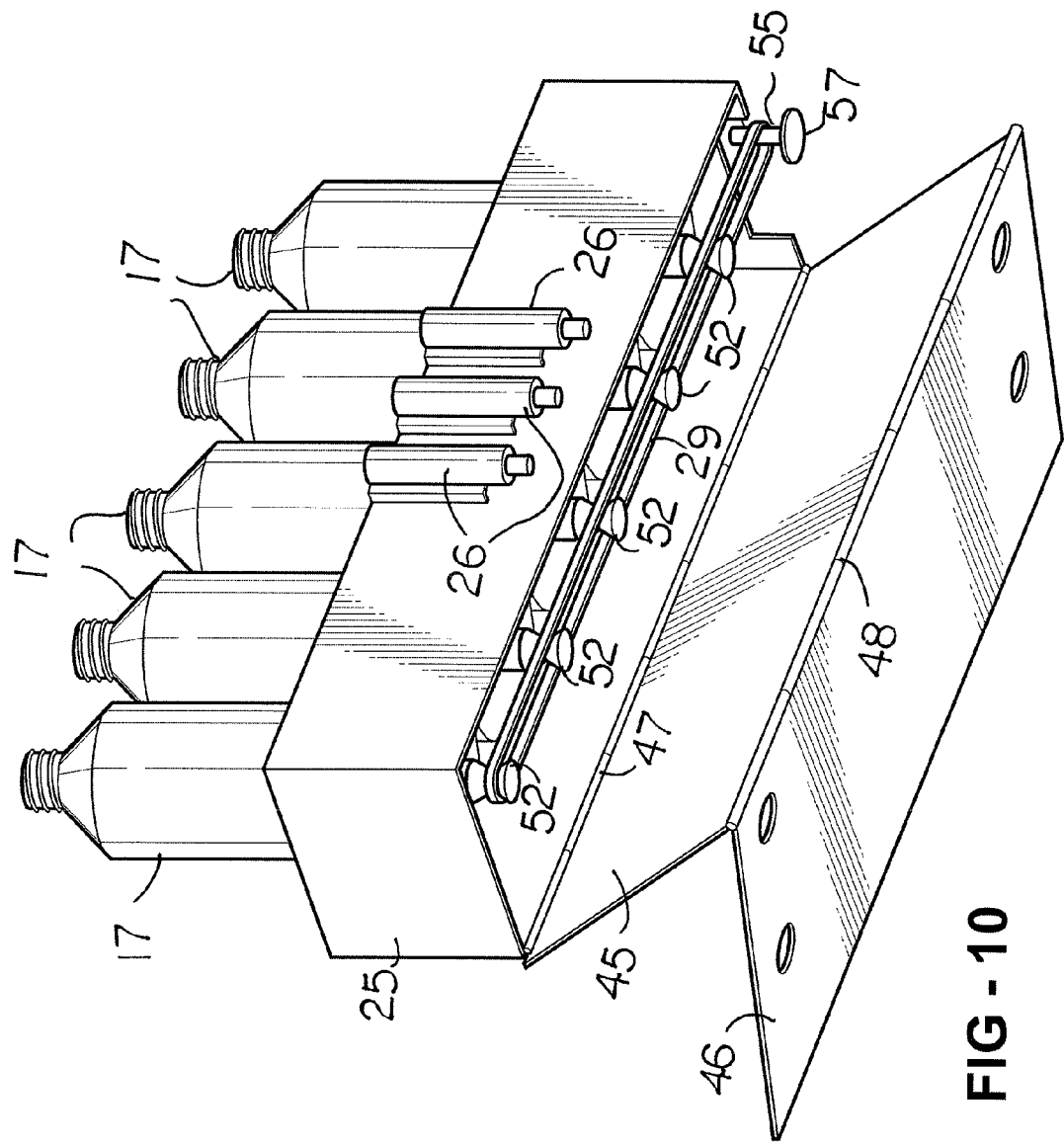
FIG. 10 is a perspective view of the bottom of the support base according to one embodiment of the present invention.

FIG. 10 is a perspective view of the bottom of the support base according to one embodiment of the present invention. The bottom of the support base 25 includes a chamber through a drive belt 29 extends about a plurality of pulleys 52. The pulleys 52 are coupled to the ends of drive shafts 53 that are coupled to container receivers 30 that are discussed in more detail below. In addition to extending about the plurality of pulleys 52, the drive belt 29 extends about a driven shaft 55 that is coupled to a motor 56. The driven shaft 55 includes a drive belt retainer 57 on the free end which prevents the drive belt 29 from coming off the driven shaft 55. When the motor 56 is activated, drive belt 29 rotates and causes rotation of the drive shafts 53 and the container receivers 30 that are coupled to the drive shafts 53. The container receivers 30 can be made from a material such as a soft plastic or hard rubber material that can create a frictional engagement with the containers 17 so as to cause the containers 17 to rotate with the container receivers 30. Alternatively, the inner walls and/or inner bottom of the container receivers 30 can be provided with strips or protrusions of material that enhance the frictional contact between the container receivers 30 and the containers 17. In further embodiments, the inner surface of the bottoms or inner walls of the container receivers 30 could be configured with structure that cooperates and engages with structure provided on the bottoms or walls of the containers 17.

Figure 11:
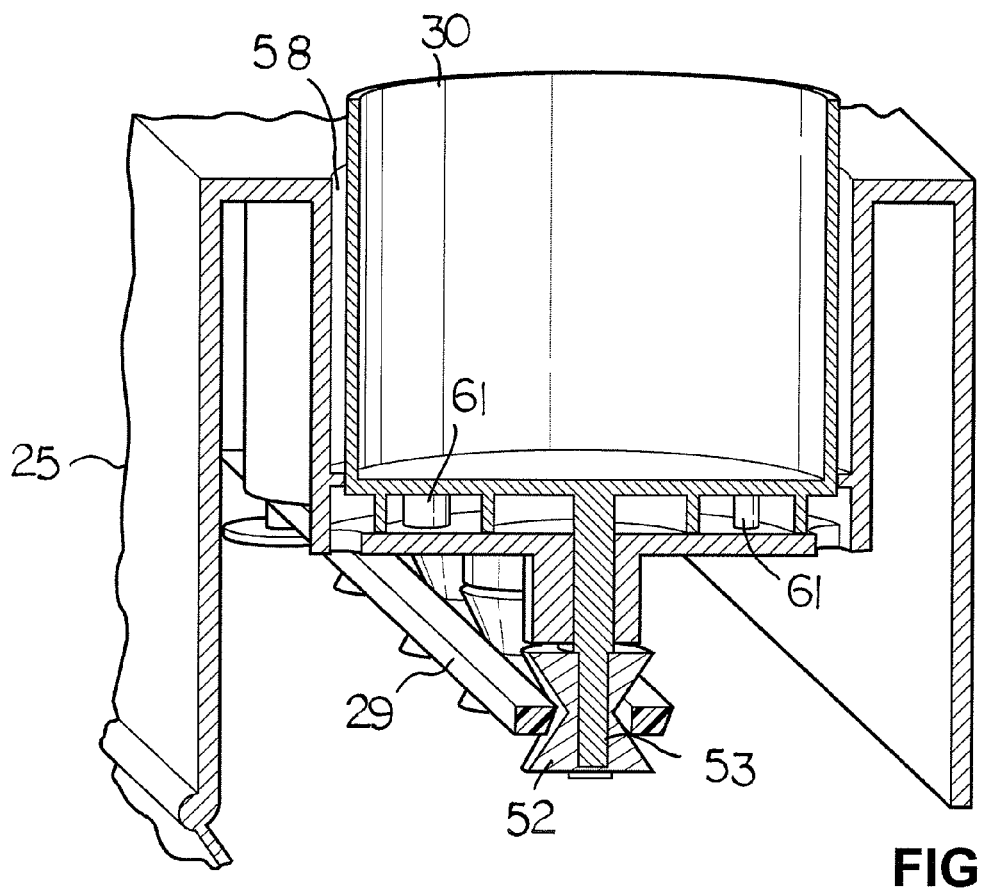
FIG. 11 is a perspective cross-sectional view through the support base and one of the container receivers according to one embodiment of the present invention.

FIG. 11 is a perspective cross-sectional view through the support base and one of the container receivers according to one embodiment of the present invention. The container receivers 30 are positioned in circular recesses formed in the support base 25 and the drive shafts 53 coupled to the bottoms of the container receivers 30 extend through the bottoms of the circular recesses. A bearing and seal can be provided between drive shaft 53 and the through-bore through which the drive shaft 53 extends. The pulley 52 provided at the end of the drive shaft 53 is complementarily shaped to receive a drive belt 29 that has a V-shaped profile as shown in FIG. 11. In other embodiments, the pulleys 52 could be configured to receive a drive belt with a D-shaped profile or any other profile shape. It is also possible to use a chain in place of drive belt 29 and provide pulleys with teeth that can be engaged with links of the chain.

Figure 12:
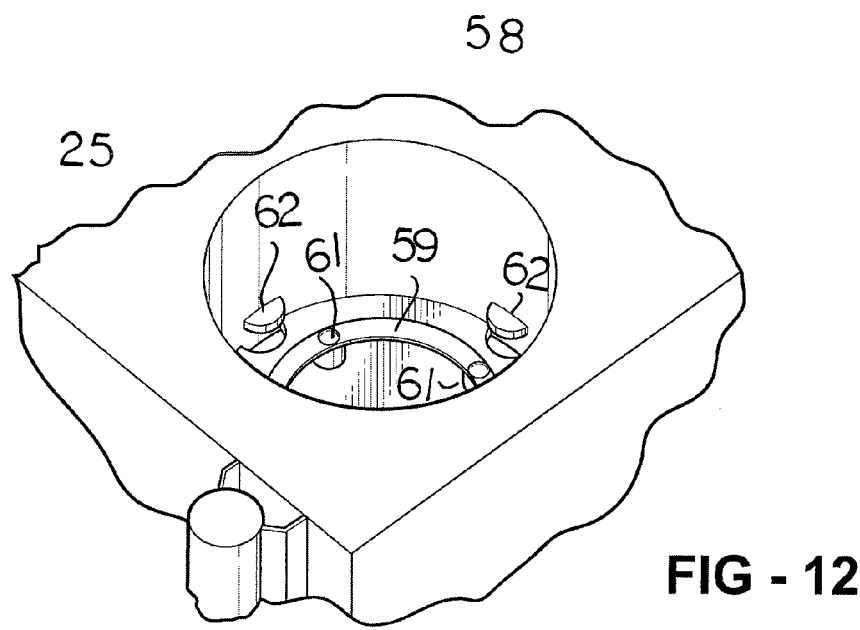
FIG. 12 is perspective view of a circular recess formed in the support base according to one embodiment of the present invention.

FIG. 12 is perspective view of a circular recess formed in the support base according to one embodiment of the present invention. At the bottom of the circular container recess 58 a bearing assembly 59 is provided that includes a cage or ring 60 that holds a plurality of ball bearings 61. The bearing assembly 59 is provided beneath the container receivers 30 as shown in FIG. 11.

FIG. 12 depicts a plurality of structures 62 that are used to engage bottom edges of the container receivers 30 and secure the container receivers 30 in the circular recesses 58. The structures 62 represent yieldable structures over which a flange on the bottoms of the container receivers 30 can be pushed to secure the container receivers 30 in the container recesses 58. Alternatively, the structures 62 could be ridge structures and the bottoms of the container receivers 30 could have yieldable flanges which can be pushed under the structures to secure the container receivers 30 in the circular container recesses 58. Other types of structures can be used to secure the container receivers 30 in the container recesses 58.

Figure 13:
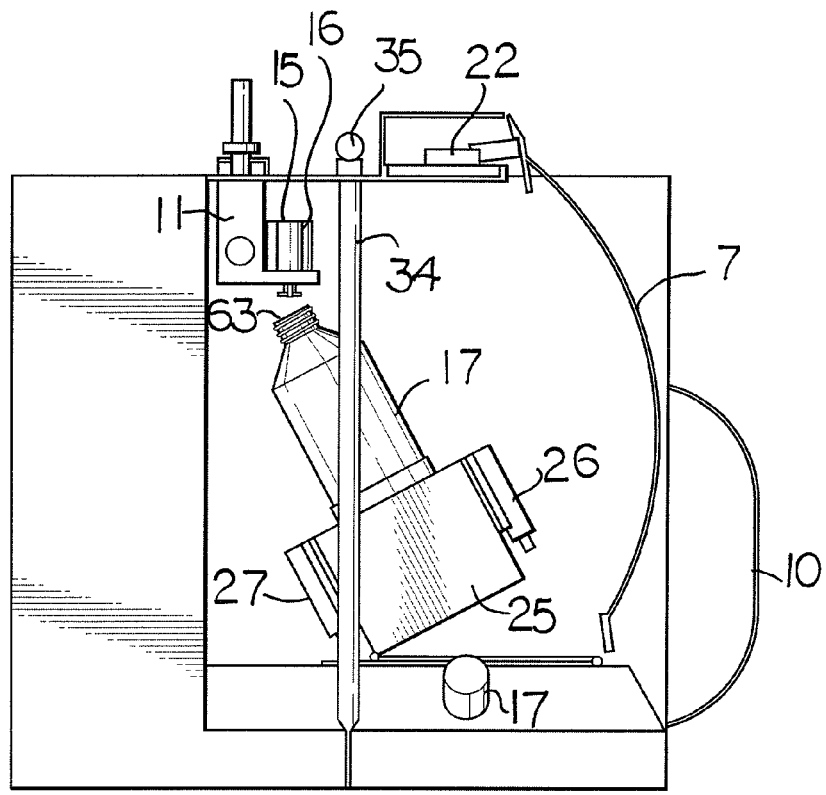
FIG. 13 is an end view of the apparatus of FIG. 1 that depicts how ingredients are dispensed into the containers from the carrier.

FIG. 13 is an end view of the apparatus of FIG. 1 that depicts how ingredients are dispensed into the containers from the carrier. In FIG. 13, the carrier 11 has moved along carrier rod 38 so as to be aligned with container 17. In addition, at least one of the front solenoids 26 has been activated so as to cause upper hinge plate 45 to pivot about hinge 47 can cause the support base 25 to incline so that the mouth 63 of the container 17 is positioned beneath the carrier 11 as shown. With the container 17 in this position, ingredients from the cylinders or cartridges 15 can be dispensed into container 17. It is noted that the UV light source 16 is also shown as being proximal to the mouth 63 of the container 17 so as to sterilize the container 17 during the process of dispensing ingredients. A similar UV light source can be used to further sterilize the containers 17 before, as of after filtered water is dispensed into the containers 17 by the filtered water dispensing spouts 36. When the UV light source 16 is aligned with the mouth 63 of the containers 17, it is possible to rotate the containers 17 to direct the UV light against the complete circumference of the inner side walls of the container 17 for purposes of sterilizing the interior of the container 17. It is also possible to reverse the rotation of the containers 17 at any time to mix ingredients dispenser therein. The manner and mechanism for rotating the containers 17 is discussed above. A UV light source can also be provided which directs UV light onto the caps 22 so as to sterilize the caps 22 before they are placed on the containers 17.

Figure 14:
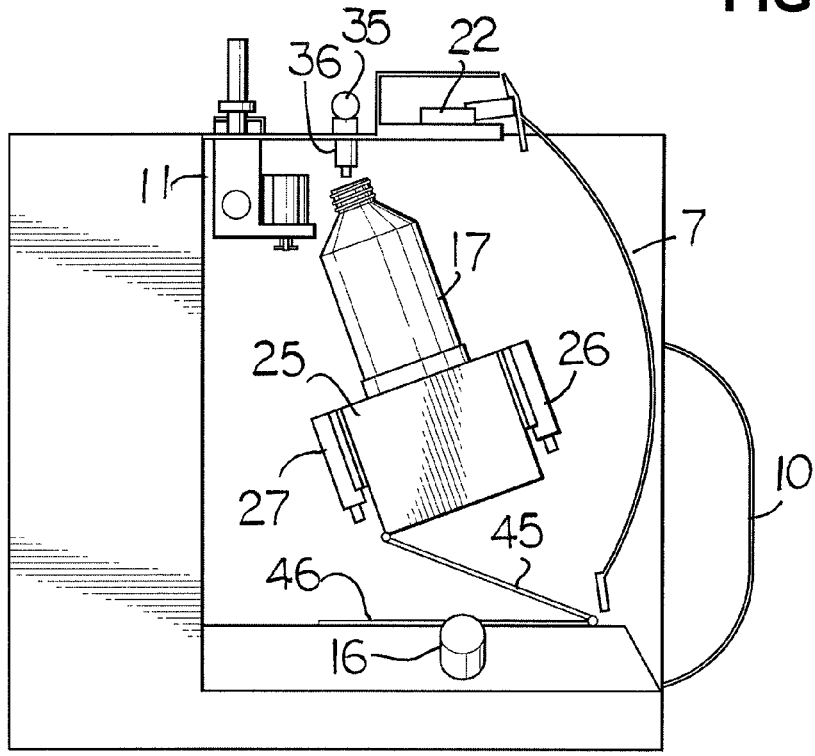
FIG. 14 is an end view of the apparatus of FIG. 13 that depicts how filtered water is dispensed into the containers.

FIG. 14 is an end view of the apparatus of FIG. 13 that depicts how filtered water is dispensed into the containers. After the ingredients from cylinders or cartridges 15 are dispensed into container 17, the solenoids 26 and 27 are activated so that the support base 25 is lifted and inclined so that the mouth 63 of the container 17 is positioned beneath one of the fluid dispensing spouts 36. In this regard, it is noted that the fluid dispensing spouts 36 are in alignment with the containers as shown in FIG. 2. With the container 17 aligned in the position shown in FIG. 14, filtered water from fluid dispensing manifold 35 can be dispensed into container 17. As discussed above, sensors 41 are used to control the filling of the containers 17 so that the containers 17 are not over-filled.

Figure 15:
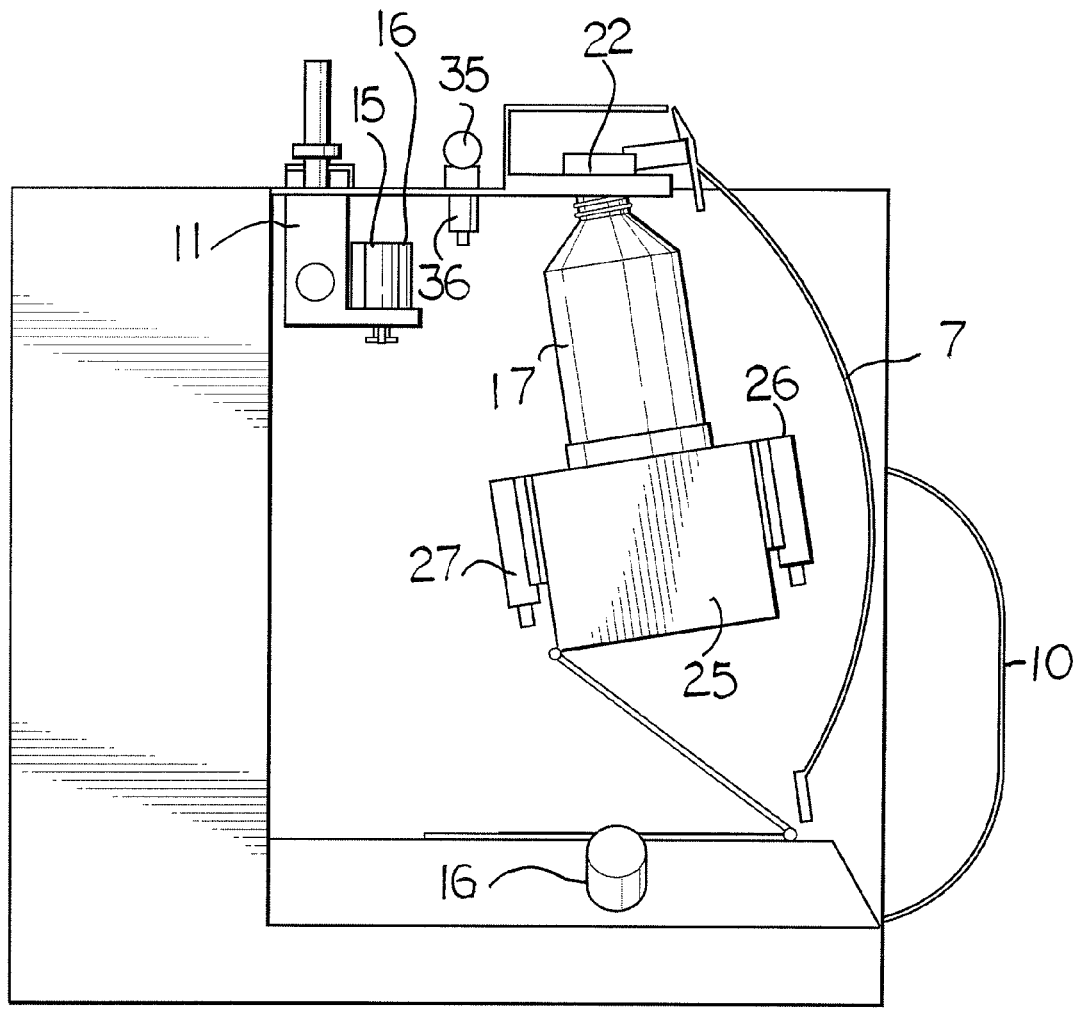
FIG. 15 is an end view of the apparatus of FIG. 14 that depicts how the caps are put onto the containers.

FIG. 15 is an end view of the apparatus of FIG. 14 that depicts how the caps are put onto the containers. After the ingredients from cylinders or cartridges 15 are dispensed into container 17 and container 17 is filled with filtered water, the solenoids 26 and 27 are activated so that the support base 25 is lifted and aligned so that the mouth 63 of the container 17 is position beneath one of the caps 22 that is held in cap retaining mechanism 19 discussed above. When the container 17 is lifted upward to engage cap 22, motor 28 is activated (See FIG. 3) so that container 17 rotates, causing cap 22 to be threaded onto container 17. As in FIGS. 13 and 14, the container 17 is lifted upward into the position shown in FIG. 15 by activating solenoids 26 and 27.

After the containers 17 are filled with filtered water and desired ingredients and the caps 22 are secured onto the containers, the solenoids 26 and 27 are deactivated and the support base 25 is lowered to the position shown in FIG. 1.

One can then open cover 7 and remove one or more of the containers 17 to drink the contents thereof.

Figure 16:
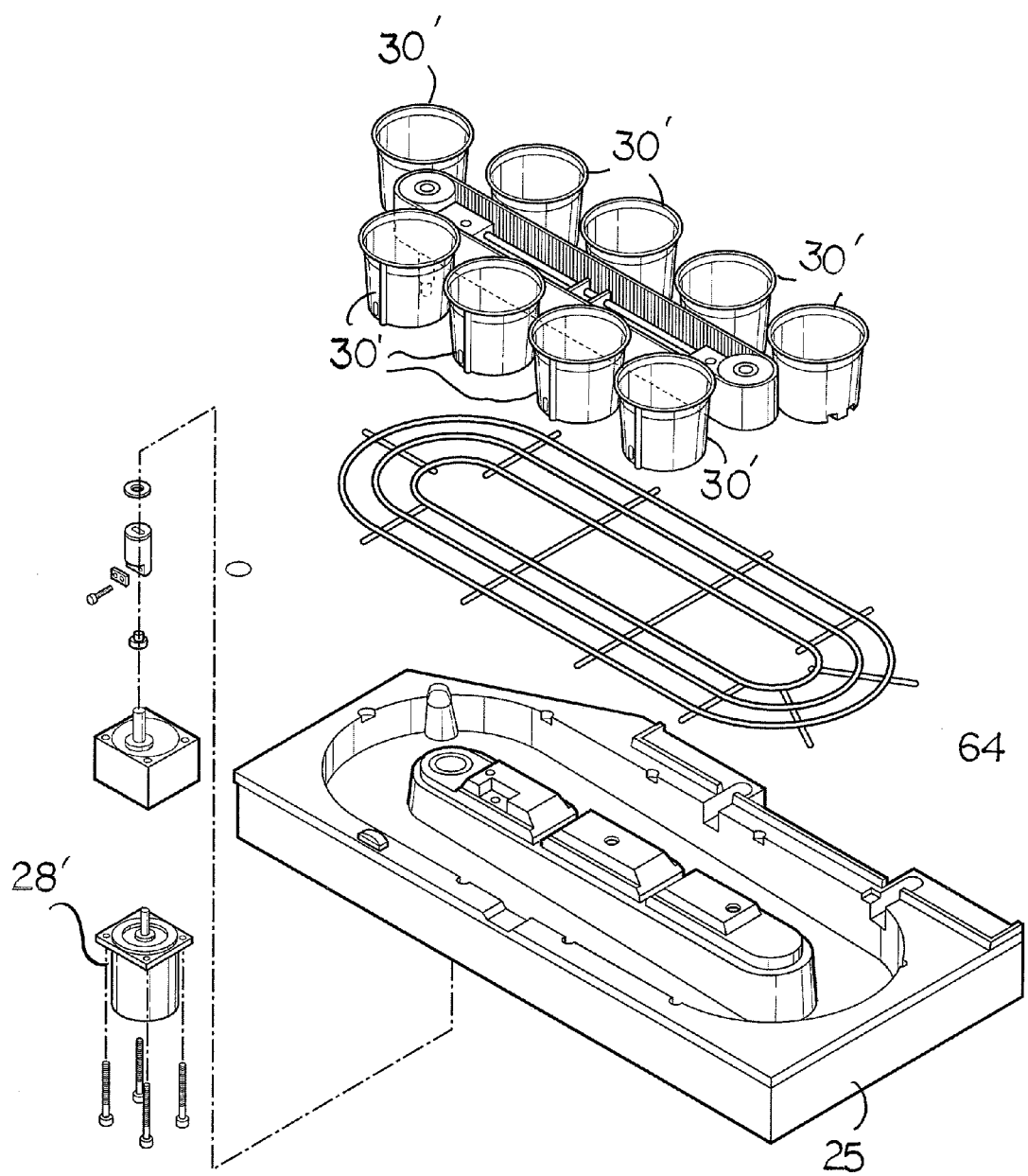
FIG. 16 is an alternative embodiment of the apparatus of the present invention.

FIG. 16 is an alternative embodiment of the apparatus of the present invention. Rather than provide the cylinders or cartridges 15 and a VU light source 16 on carrier 11 that moves with respect to the position of the individual containers 17 supported on the support base 25, the embodiment of the invention shown in FIG. 16 allows for the containers 17 to move and be positioned beneath cylinders or cartridges and a VU light source(s) that can be provided in fixed positions (not shown). In the embodiment of the invention shown in FIG. 16, the support base 25' is provided with a plurality of container receivers 30' that are coupled to a belt 29' that can be driven by motor 28' to move containers 17 (not shown) positioned in the container receivers 30' to any position along the illustrated path at which the cylinders or cartridges and a VU light source(s) can be provided as well as a filtered water dispensing spout(s). The motor 28' can be a step motor that can be controlled in a conventional manner to move the containers 17 from station to station. A friction reducing track support 64 is shown as being positioned beneath the container receivers 30'. The support base 25' shown in FIG. 16 can be articulated upward and inclined by hinge plates similar to those shown in FIG. 9. Caps 22 could be pressed onto the filled containers 17 or threaded onto the containers 17 by rotating the container receivers 30'. In this regard, the container receivers 30' could be individually rotatably coupled to belt 29' and rotated by drive shafts that can rise up and engage the lower portions or bottoms of the container receivers 30' when the container receivers 30' are at a capping station or capping position.

Figure 17:
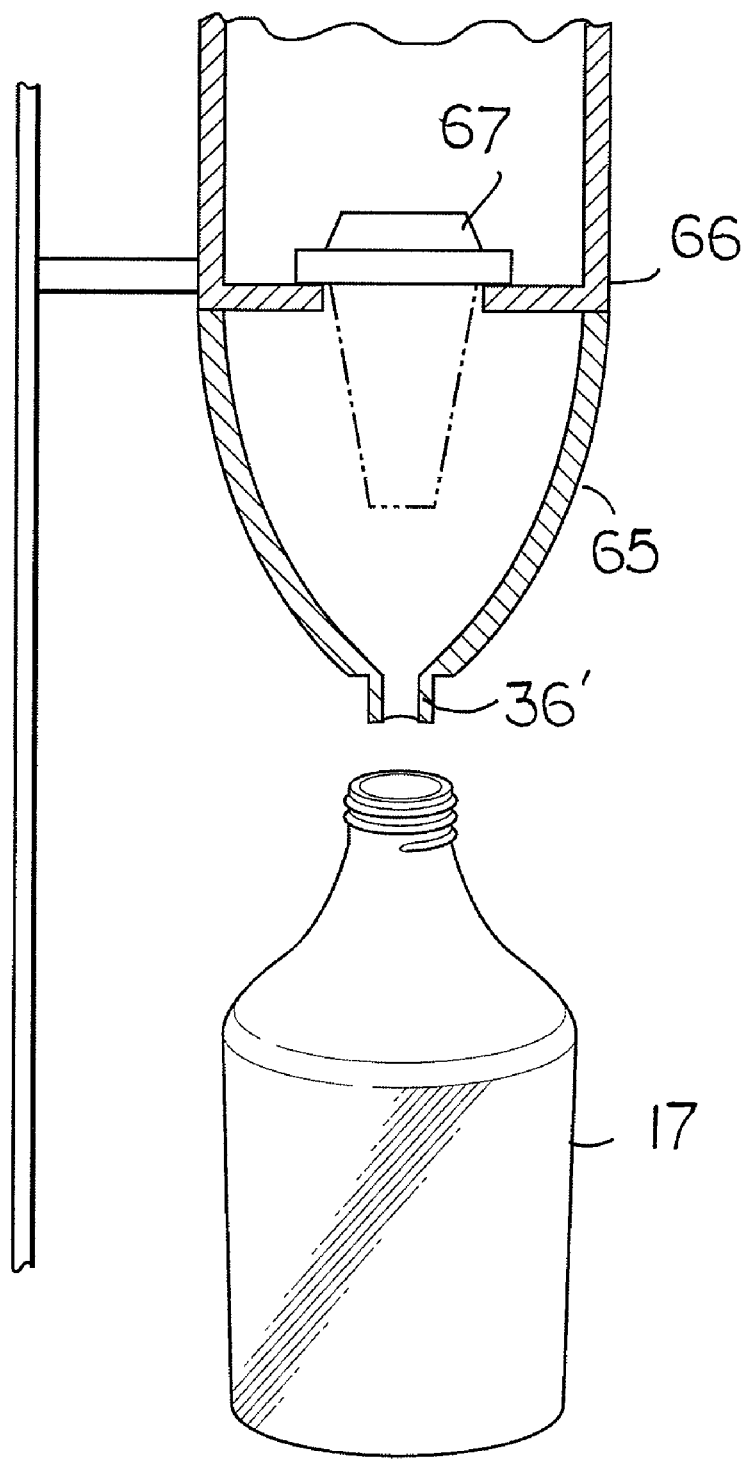
FIG. 17 is a cross-section of an alternative manner of providing filtered water according to the present invention.

FIG. 17 is a cross-section of an alternative manner of providing filtered water according to the present invention. In FIG. 7 filtered water dispensing spout 36' is provided on a lower portion of a filtered water reservoir 65 that would be positioned above the containers 17 shown FIG. 1. Above filtered water reservoir 65 is an unfiltered water reservoir 66 into which unfiltered water is added or supplied. Between the unfiltered water reservoir 66 and the filtered water reservoir 65 is one or more replaceable water filters 67 are provided. In this embodiment, the unfiltered water reservoir 66 and filtered water reservoir 65 can be provided above the containers 17. A plurality of the devices shown in FIG. 17 could be provided in the apparatus of FIG. 1. In addition, more than one filtered water dispensing spout 36 could be provided so as to develop filtered water filling stations for a plurality of containers 17. Each filtered water dispensing spout 36' would be associated with a sensor as discussed above and could also be associated with a source of UV light as discussed above.

The apparatus of the present invention can be provided with a cooling system to provide the water based beverage at a desired cool temperature for consuming. In this regard, a standard refrigeration system couple be included. In other embodiments, electronic cooling chips like the type used in automobile cup holders can be provided within the dispensing chamber 6 and/or in proximity to the filtered water reservoir 18 and/or manifold 35. In other embodiments, heating systems, including electronic heating chips or resistance heaters, or other types of heating systems and device could be included to provide room warm or even hot water-based beverages, including teas and coffees.

In further embodiments, pressed on caps or snap on caps could be used rather than screw on caps. It is also possible to stack a plurality of caps into sleeves, magazines, chutes, etc. rather than use the jaw elements as the only means to position and secure the caps.

Although the present invention has been described with reference to particular means, materials and embodiments, from the foregoing description, one skilled in the art can easily ascertain the essential characteristics of the present invention and various changes and modifications can be made to adapt the various uses and characteristics without departing from the spirit and scope of the present invention as described above.

What is claimed is:

1. An apparatus producing a water-based beverage that comprises:
    a first dispenser for dispensing coupled to a source of at least one of an ingredient selected from the group consisting of nutrients, health supplements, caffeine, flavorings, vitamins, sweeteners, coloring agents and medicines;
    a second dispenser coupled to a source of water;
    a container capping mechanism including a supply of container caps;
    at least one container on a support base, which support base is coupled to an upper and lower hinge plate;
    means for moving at least one of the support base and the first dispenser so that the at least one container is aligned with the first dispenser for dispensing one of the ingredients into the at least one container;
    means for moving at least one of the support base and the second dispenser so that the at least one container is aligned with the second dispenser for dispensing water into the at least one container; and
    means for moving at least one of the support base and the capping mechanism so that the at least one container is aligned with the capping mechanism for putting a cap on the at least one container.

2. An apparatus producing a water-based beverage according to claim 1, further comprising a housing in which the first dispenser, second dispenser, capping mechanism and support base are housed.

3. An apparatus producing a water-based beverage according to claim 1, wherein the housing includes a water reservoir and a compartment that contains a removable container.

4. An apparatus producing a water-based beverage according to claim 2, wherein the housing includes an unfiltered water reservoir and a filtered water reservoir that are coupled to a common water filter.

5. An apparatus producing a water-based beverage according to claim 1, wherein the support base includes means for rotating the at least one container.

6. An apparatus producing a water-based beverage according to claim 1, wherein the first dispenser comprises a carrier that moves linearly.

7. An apparatus producing a water-based beverage according to claim 1, wherein the second dispenser comprises at least one dispensing spout and at least one sensor that senses fluid level in the at least one container as water is dispensed into the at least one container.

8. An apparatus producing a water-based beverage according to claim 1, further comprising a UV light source that irradiates an inside portion of the at least one container.

9. An apparatus producing a water-based beverage according to claim 8, further comprising a UV light source that irradiates the filtered water reservoir.

10. An apparatus producing a water-based beverage that comprises:
    a first dispenser for dispensing coupled to a source of at least one of an ingredient selected from the group consisting of nutrients, health supplements, caffeine, flavorings, vitamins, sweeteners, coloring agents and medicines;

a second dispenser coupled to a source of water, said second dispenser comprising least one dispensing spout and at least one sensor that senses fluid level in the at least one container as water is dispensed into the at least one container;

a container capping mechanism including a supply of container caps;

at least one container on a support base;

means for moving at least one of the support base and the first dispenser so that the at least one container is aligned with the first dispenser for dispensing one of the ingredients into the at least one container;

means for moving at least one of the support base and the second dispenser so that the at least one container is aligned with the second dispenser for dispensing water into the at least one container; and means for moving at least one of the support base and the capping mechanism so that the at least one container is aligned with the capping mechanism for putting a cap on the at least one container.

11. An apparatus producing a water-based beverage according to claim 10, further comprising a housing in which the first dispenser, second dispenser, capping mechanism and support base are housed.

12. An apparatus producing a water-based beverage according to claim 11, wherein the housing includes a water reservoir and a compartment that contains a removable container.

13. An apparatus producing a water-based beverage according to claim 11, wherein the housing includes an unfiltered water reservoir and a filtered water reservoir that are coupled to a common water filter.

14. An apparatus producing a water-based beverage according to claim 10, wherein the support base includes means for rotating the at least one container.

15. An apparatus producing a water-based beverage according to claim 10, wherein the first dispenser comprises a carrier that moves linearly.

16. An apparatus producing a water-based beverage according to claim 10, wherein the support base is coupled to an upper and lower hinge plate.

17. An apparatus producing a water-based beverage according to claim 10, further comprising a UV light source that irradiates an inside portion of the at least one container.

18. An apparatus producing a water-based beverage according to claim 13, further comprising a UV light source that irradiates the filtered water reservoir.

19. An apparatus producing a water-based beverage according to claim 10, wherein the at least one container moves along the support base.

* * * * *

UNITED STATES PATENT AND TRADEMARK OFFICE
CERTIFICATE OF CORRECTION

PATENT NO. : 8,069,774 B2
APPLICATION NO. : 12/059083
DATED : December 6, 2011
INVENTOR(S) : Robert Mazur It is certified that error appears in the above-identified patent and that said Letters Patent is hereby corrected as shown below:

In the Specification

Column 1, line 18, after the partial word "ally", insert -- flavored or fortified filter water. --

Column 1, line 59, after "moving one of the support base and the", insert -- first dispenser --

Column 1, lines 64-67, should be deleted.

Column 7, line 8, the last word "font" should be replaced with -- front --

Signed and Sealed this
Fifth Day of June, 2012

David J. Kappos
*Director of the United States Patent and Trademark Office*